(12) United States Patent
Kang et al.

(10) Patent No.: US 12,054,760 B2
(45) Date of Patent: Aug. 6, 2024

(54) **HIGH-EFFICIENCY SYNTHESIS AND HIGH-PURITY HYALURONIC ACID, AND RECOMBINANT *CORYNEBACTERIUM GLUTAMICUM* FOR OLIGOSACCHARIDE THEREOF**

(71) Applicants: BLOOMAGE BIOTECHNOLOGY CORPORATION LIMITED, Jinan (CN); JIANGNAN UNIVERSITY, Wuxi (CN)

(72) Inventors: Zhen Kang, Wuxi (CN); Jian Chen, Wuxi (CN); Litao Hu, Wuxi (CN); Guocheng Du, Wuxi (CN); Yang Wang, Wuxi (CN); Jianghua Li, Wuxi (CN); Jialian Li, Wuxi (CN); Tianmeng Zhang, Jinan (CN)

(73) Assignees: BLOOMAGE BIOTECHNOLOGY CORPORATION LIMITED, Jinan (CN); JIANGNAN UNIVERSITY, Wuxi (CN)

( * ) Notice: Subject to any disclaimer, the term of this patent is extended or adjusted under 35 U.S.C. 154(b) by 6 days.

(21) Appl. No.: 17/755,191

(22) PCT Filed: Dec. 17, 2019

(86) PCT No.: PCT/CN2019/126013
§ 371 (c)(1),
(2) Date: Apr. 22, 2022

(87) PCT Pub. No.: WO2021/077580
PCT Pub. Date: Apr. 29, 2021

(65) Prior Publication Data
US 2022/0380819 A1 Dec. 1, 2022

(30) Foreign Application Priority Data
Oct. 24, 2019 (CN) .................. 201911018182.4

(51) Int. Cl.
C12P 19/04 (2006.01)
C12N 1/20 (2006.01)
C12N 9/10 (2006.01)
C12N 9/26 (2006.01)
C12N 15/77 (2006.01)
C12R 1/15 (2006.01)

(52) U.S. Cl.
CPC ............. *C12P 19/04* (2013.01); *C12N 1/205* (2021.05); *C12N 9/1051* (2013.01); *C12N 9/2474* (2013.01); *C12N 15/77* (2013.01); *C12Y 204/01212* (2013.01); *C12Y 302/01035* (2013.01); *C12N 2800/101* (2013.01); *C12R 2001/15* (2021.05)

(58) Field of Classification Search
None
See application file for complete search history.

(56) References Cited

U.S. PATENT DOCUMENTS 9,670,514 B2  6/2017  Yanagihara et al.

FOREIGN PATENT DOCUMENTS

| CN | 101709285 A | 5/2010 |
|----|-------------|--------|
| CN | 103597088 A | 2/2014 |
| CN | 103937734 A | 7/2014 |
| CN | 106190939 A | 12/2016 |
| CN | 107354119 A | 11/2017 |
| CN | 108251346 A | 7/2018 |
| WO | WO 03/060063 A2 | 7/2003 |

OTHER PUBLICATIONS

Accession Q5X9A9. Aug. 30, 2005 (Year: 2005).*
Chica et al. Curr Opin Biotechnol. Aug. 2005; 16(4):378-84. (Year: 2005).*
Singh et al. Curr Protein Pept Sci. 2017, 18, 1-11 (Year: 2017).*
Taniguchi et al. BMC Microbiol 17, 158 (2017). (Year: 2017).*
CN103937734. Jul. 23, 2014, English machine translation. (Year: 2014).*
Cheng et al., "Enhanced Biosynthesis of Hyaluronic Acid Using Engineered Corynebacterium glutamicum via Metabolic Pathway Regulation," Biotechnol J, vol. 12, No. 10, 1 page, (2017), Abstract Only.
Weigel et al., "Hyaluronan Synthases: A Decade-plus of Novel Glycosyltransferases," The Journal of Biological Chemistry, vol. 282, No. 51, p. 36777-36781, (2007).
Wang, Y. et al., "Eliminating the capsule-like layer to promote glucose uptake for hyaluronan production by engineered Corynebacterium Glutamicum," Nature Communications, vol. 11, No. 3120, 10 pages, (2020).
Westbrook, A. et al., "Metabolic engineering to enhance heterologous production of hyaluronic acid in Bacillus subtilis," Metabolic Engineering, vol. 47, pp. 401-413, (2018).

* cited by examiner

*Primary Examiner* — Christian L Fronda
(74) *Attorney, Agent, or Firm* — Hoxie & Associates LLC

(57) ABSTRACT

The invention discloses a recombinant *Corynebacterium glutamicum* for efficient synthesis of highly pure hyaluronic acid and oligosaccharides thereof, belonging to the technical field of bioengineering. The recombinant *Corynebacterium glutamicum* constructed in the present invention can produce hyaluronic acid with a yield up to 40 g/L, and a crude product purity of 95%. Addition of exogenous hyaluronic acid hydrolase and optimization of the fermentation conditions results in hyaluronic acid oligosaccharides with specific molecular weight, and can further improve the yield of hyaluronic acid to 72 g/L. The invention lays a solid foundation for the efficient synthesis of highly pure hyaluronic acid by microorganisms, and the constructed recombinant *Corynebacterium glutamicum* is suitable for industrial production and application.

9 Claims, 2 Drawing Sheets

Specification includes a Sequence Listing.

HIGH-EFFICIENCY SYNTHESIS AND HIGH-PURITY HYALURONIC ACID, AND RECOMBINANT *CORYNEBACTERIUM GLUTAMICUM* FOR OLIGOSACCHARIDE THEREOF

CROSS REFERENCE TO RELATED APPLICATIONS

This application is a United States Application under 35 U.S.C. 371 claiming benefits of PCT Application No. PCT/CN2019/126013, filed on Dec. 17, 2019, which claims the benefit of priority from Chinese Patent Application No. 201911018182.4, filed on Oct. 24, 2019, the contents of each of which are incorporated herein by reference.

FIELD OF THE INVENTION

The invention relates to a recombinant *Corynebacterium glutamicum* for efficient synthesis of highly pure hyaluronic acid and oligosaccharides thereof, belonging to the technical field of bioengineering.

BACKGROUND OF THE INVENTION

Hyaluronic acid is a straight-chain acidic mucopolysaccharide made by polymerizing disaccharide units composed of N-acetylglucosamine and glucuronic acid. Hyaluronic acid with ultra-high molecular weight has functions such as good viscoelasticity, moisturizing and anti-inflammatory properties, and can be used as a viscoelastic agent in ophthalmic surgery, for therapy via intra-articular injection, and the like. Hyaluronic acid with high molecular weight has good moisturizing and lubricating effects and can be used in the field of cosmetics. Hyaluronic acid and oligosaccharides thereof with high purity have effects on, such as anti-tumor, promoting wound healing, promoting osteogenesis and angiogenesis, and regulating immune. In 2016, the global market for hyaluronic acid was US$ 7.2 billion, and it is predicted that the global value will reach US$10.8 billion in 2020.

At present, the commercially available hyaluronic acid is mainly obtained by the fermentation of *Streptococcus zooepidemicus*, which naturally produces hyaluronic acid. However, the hyaluronic acid produced by *Streptococcus zooepidemicus* is difficult to meet the requirements of medicine, food and other fields, since *Streptococcus zooepidemicus* is a pathogenic strain and can cause many diseases. Furthermore, the hyaluronic acid produced therefrom has low purity, reducing the quality of the product. In order to solve this problem, genetic engineering technology was used to synthesiz hyaluronic acid by heterologous expression of hyaluronan synthase in some engineered strains, such as *Bacillus subtilis* and *Corynebacterium glutamicum*. However, *Bacillus subtilis* itself is prone to cell lysis, and the DNA released from cell lysis will cause contamination to the hyaluronic acid product. In comparison, *Corynebacterium glutamicum* has thicker cell walls, stronger tolerance, and better cell stability than *Bacillus subtilis*. However, *Corynebacterium glutamicum* will synthesize more exopolysaccharides outside the cell. These polysaccharides not only compete for substrates in the hyaluronic acid synthesis pathway, but also increase the difficulty in the downstream purification of hyaluronic acid, thereby reducing the quality of the hyaluronic acid product.

SUMMARY OF THE INVENTION

The first purpose of the present invention is to provide a recombinant *Corynebacterium glutamicum*, for which the exopolysaccharide gene cg0420 and/or cg0424 are/is silenced or knocked out, and hyaluronan synthase is expressed; the gene cg0420 comprises nucleotide sequence as shown in SEQ ID NO.1; the cg0424 comprises nucleotide sequence as shown in SEQ ID NO.2; and the hyaluronan synthase is as shown in (a), (b) or (c):

(a) an enzyme derived from *Streptococcus pyogenes* and the amino acid sequence thereof having at least 90% homology to SEQ ID NO.3;
(b) an enzyme having amino acid sequence as shown in SEQ ID NO.3;
(c) a protein derived from (a) or (b) that is substituted or deleted on the basis of (a) or (b) and having hyaluronan synthase activity.

In one embodiment, the exopolysaccharide genes cg0420 (SEQ ID NO. 1) and cg0424 (SEQ ID NO. 2) of the recombinant *Corynebacterium glutamicum* are silenced or knocked out and hyaluronan synthase is expressed in the recombinant *Corynebacterium glutamicum*.

In one embodiment, the hyaluronan synthase is derived from *Streptococcus pyogenes* (SEQ ID NO. 3).

In one embodiment, the UDP-N-acetylglucosamine and/or UDP-glucuronic acid pathway are/is enhanced in the *Corynebacterium glutamicum*.

In one embodiment, the UDP-N-acetylglucosamine pathway comprises: glutamine-fructose-6-phosphate aminotransferase, phosphoglucomutase, UDP-N-acetylglucosamine pyrophosphorylase/glucose-1-phosphate acetyltransferase bifunctional enzyme.

In one embodiment, the UDP-glucuronic acid pathway comprises: phosphoglucomutase, glucose-6-phosphate uramidotransferase, UDP-glucose dehydrogenase.

In one embodiment, the phosphoglucomutase pgm (SEQ ID NO.4), glucose-6-phosphate uramidotransferase GalU (SEQ ID NO.5), UDP-glucose dehydrogenase Ugd (SEQ ID NO.6), glutamine-fructose-6-phosphate aminotransferase GlmS (SEQ ID NO.7), phosphoglucomutase GlmM (SEQ ID NO.8), UDP-N-acetylglucosamine pyrophosphorylase/glucose-1-phosphate acetyltransferase bifunctional enzyme GlmU (SEQ ID NO.9) are derived from *Pseudomonas putida* KT2440.

In one embodiment, the expression of at least one gene selected from pgM, ugd, galU, glms, glmM and glmU is enhanced in any of the above-mentioned *Corynebacterium glutamicum*.

In one embodiment, the recombinant *Corynebacterium glutamicum* is derived from an industrially safe strain *Corynebacterium glutamicum*, heterologously expresses the hyaluronan synthase gene hasA derived from *Streptococcus pyogenes*; the *Corynebacterium glutamicum* exopolysaccharide genes cg0420 and cg0424 of the recombinant *Corynebacterium glutamicum* are knocked out to remove heteropolysaccharides from the extrocytoplasmic surface; and expression cassettes are constructed to enhance the expressions of pathway genes pgM, ugd, galU, glms, glmM and glmU, thereby increasing the production of synthetic substrates for hyaluronic acid—UDP-N-acetylglucosamine and UDP-glucuronic acid.

In one embodiment, any one of the above-mentioned *Corynebacterium glutamicum* also expresses *Vitreoscilla* hemoglobin VHb (SEQ ID NO. 10) to improve the growth of recombinant *Corynebacterium glutamicum* in microaerobic environment and the ability to synthesize hyaluronic acid. The second purpose of the present invention is to provide a method for constructing the recombinant *Corynebacterium glutamicum*, the method comprising: (1) knocking out exopolysaccharide synthesis genes cg0420 and cg0424 stepwise or simultaneously by constructing knock-out box(es); (2) ligating hyaluronan synthase-encoding gene and at least one gene selected from pgM, ugd, gal U, glmS, glmM and glmU to a vector, which is in turn transformed into the strain cell of interest.

In one embodiment, the vector may be pXMJ19, pECXK99E, pEC-XT99A, pEKEx1, pEKEx2, pVWEx1, pVWEx2, pZ8-1, pECTAC-K99 or pAPE12 (the above vectors are disclosed in Eggeling, L. and Bott, M., Handbook of *Corynebacterium glutamicum*. 2005, Boca Raton: Taylor & Francis. 616 p).

In one embodiment, the method relates to ligating pgm, galU, ugd to the vector pXMJ19.

In one embodiment, the method relates to ligating glmS, glmM, glmU to the vector pECXK99E.

The third purpose of the present invention is to provide a method for producing hyaluronic acid, the method comprises fermenting the recombinant *Corynebacterium glutamicum*.

In one embodiment, the fermentation is performed at 25-35° C. for 24-72 h.

In one embodiment, the method also involves the addition of a hyaluronan hydrolase or hyaluronan lyase in the early stage of the fermentation; the hyaluronan hydrolase or hyaluronan lyase is added at an amount of 500-50000 U/mL.

The fourth purpose of the present invention is to provide a use of the recombinant *Corynebacterium glutamicum* in the preparation of hyaluronic acid and derivative products thereof.

Beneficial effect: in the present invention, a synthesis pathway of hyaluronic acid is constructed in the industrially safe strain *Corynebacterium glutamicum*, which heterologously expresses hyaluronan synthase gene hasA derived from *Streptococcus pyogenes*. The purity of hyaluronic acid is improved by knocking out the *Corynebacterium glutamicum* exopolysaccharide genes cg0420 and cg0424 and thereby removing the heteropolysaccharides from the extrocytoplasmic surface. The ability of the recombinant *Corynebacterium glutamicum* to synthesize hyaluronic acid is improved by constructing expression cassettes to enhance the expressions of pathway genes pgM, ugd, galU, glms, glmM and glmU, which increases the synthesis of UDP-N-acetylglucosamine and UDP-glucuronic acid, as synthetic substrates for hyaluronic acid, and thereby solves the problem of insufficient supply of substrates during the synthesis of hyaluronic acid. In order to solve the problem of insufficient dissolved oxygen during the fermentation process, *Vitreoscilla* hemoglobin VHb is also expressed in the recombinant *Corynebacterium glutamicum* to improve the growth of the recombinant *Corynebacterium glutamicum* in microaerobic environment and the ability to synthesize hyaluronic acid. By knocking out cg0420, both the yield and purity of hyaluronic acid have been improved to a certain extent. The yield of the crude product is increased by 27.8%, from 18 g/L to 23 g/L, and the purity is increased from 75% to 86%. By knocking out both cg0420 and cg0424, the yield of hyaluronic acid is increased by 58.3%, reaching 28.5 g/L, and the purity of crude product reaches 95%. By double knockout plus VHb expression, the production capacity of the recombinant *Corynebacterium glutamicum* reaches 40 g/L, which is increased by 40.3% compared to the original strain. The production of the oligosaccharides of hyaluronic acid is achieved by adding 6000 U/mL exogenous hyaluronic acid hydrolase during the fermentation process. Finally, the capacity for the production of hyaluronic acid reaches 72 g/L, which is increased by 152.6% compared to the original strain and is 2.5 times higher than that of the highest-producing strain reported so far.

DETAILED DESCRIPTION OF THE INVENTION

Figure 1:
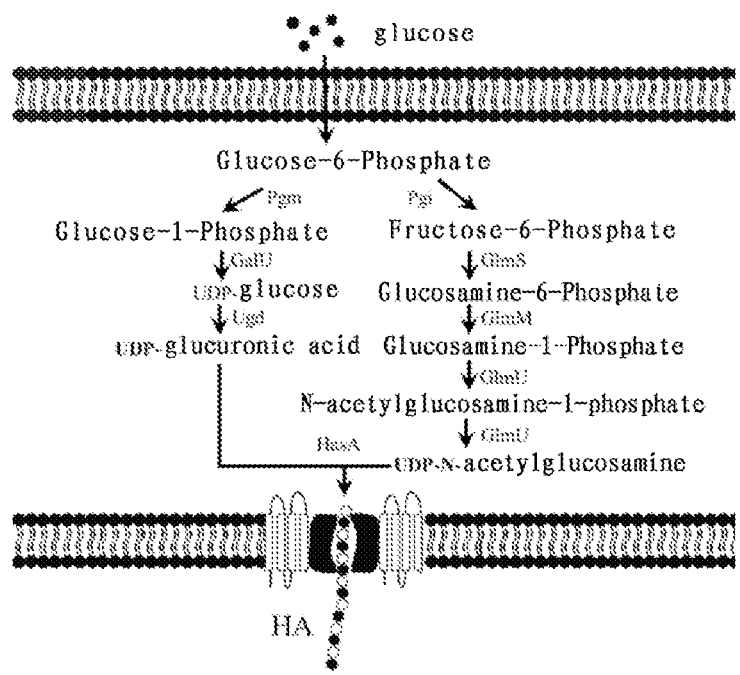
FIG. 1: Metabolic pathways and related enzymes for the production of hyaluronic acid by the recombinant *Corynebacterium glutamicum*.

Strain: *Corynebacterium glutamicum* ATCC 13032, plasmids: pXMJ19, pEC-XK99E, pK18mobSacB LB medium: Yeast powder 5 g/L, peptone 10 g/L, and sodium chloride 10 g/L BHI: Brain heart extract 17 g/L, sorbitol 21 g/L Fermentation Medium: Glucose: 40 g/L, corn steep powder: 20 g/L, $KH_2PO_4$: 15 g/L, $K_2HPO_4$: 5 g/L, $MgSO_4$: 1 g/L.

Determination of the hyaluronic acid yield: The fermentation broth was taken appropriately and 10-fold diluted, centrifuged at 10,000 rpm for 10 minutes, the supernatant was taken and added with 4× volume of pre-cooled ethanol, placed at −20 for 6h-ethanol precipitation, centrifuged at 10,000 rpm for 10 minutes, the supernatant was discarded, resuspended with water up to the original volume, centrifuged at 10,000 rpm for 5 minutes, the precipitation was discarded and the supernatant was taken and added with 4× volume of pre-cooled ethanol, placed at −20 for 6h-ethanol precipitation, centrifuged at 10,000 rpm for 10 minutes, the supernatant was discarded, resuspended with water up to the original volume, centrifuged at 10,000 rpm for 5 minutes, the supernatant was taken and the precipitation was discarded. The supernatant was taken and 50-fold diluted, up to the final dilution of 500-fold. For the measurement of the sample, the sample was diluted according to the linear effective range, and then measured by the sulfuric acid carbazole method.

Determination by sulfuric acid carbazole method: 1 ml sample was added to a glass tube containing 5 mL of borax sulfuric acid (4.77 g borax dissolved in 500 mL of concentrated H2SO4), mixed well, boiled in a boiling water bath for 15 min, and cooled on ice. 250 µL of carbazole reagent (0.125 g carbazole dissolved in 100 mL absolute ethanol) was added, mixed well, and boiled in a boiling water bath for 15 min. The blank control was prepared in the same condition, except the sample was replaced with an equal volume of distilled water, and the absorbance value at the wavelength of 530 nm was measured. Different concentrations (10, 20, 30, 40, 50 µg mL$^{-1}$) of D-glucuronic acid were used as standard samples to plot a standard curve, and then the content of hyaluronic acid was calculated by fitting the absorbance value thereof to the standard curve. Standard curve equation: y=126.88x−9.2639, $R^2$=0.9991 (x, A530 absorbance; y, glucuronic acid content in the sample (μg $mL^{-1}$)). Calculation formula for the yield of chondroitin: hyaluronic acid content (g/L)=(concentration determined by the standard curve*dilution factor*2.067)/1000. For the measurement of the sample, the sample was diluted according to the linear effective range.

Determination of the molecular weight of hyaluronic acid: The supernatant of the fermentation was removed impurities by repeated alcohol precipitation to obtain high-purity hyaluronic acid, which was measured by HPLC for the molecular weight.

LC-MS Determination of the Structure of Hyaluronic Acid. The supernatant of the fermentation was removed impurities by repeated alcohol precipitation to obtain high-purity hyaluronic acid, and then the sample was treated overnight at 37° C. by hyaluronidase to cleave hyaluronic acid into disaccharide units. Then, nine times the volume of anhydrous methanol was added to the sample. The impurities and unhydrolyzed hyaluronic acid were removed by centrifugation and the insoluble impurities were filtered out through an organic membrane prior to analyzing the structure of the disaccharide units by LC-MS.

Example 1

Construction of the Recombinant *Corynebacterium glutamicum*

(1) Genes cg0420 and cg0424 Knockout

A fragment about 500 bp upstream to cg0420, 0420-up, was obtained by PCR, with the genomic DNA of *Corynebacterium glutamicum* ATCC13032 as a template, and using 0420-up-F and 0420-up-R as primers, and the PCR product was purified;

A fragment about 500 bp downstream to cg0420, 0420-down, was obtained by PCR, with the genomic DNA of *Corynebacterium glutamicum* ATCC13032 as a template, and using 0420-down-F and 0420-down-R as primers, and the PCR product was purified;

The *Corynebacterium glutamicum* suicide plasmid pK18mobsacB was double digested with EcoRI/BamhI, and the 0420-up and 0420-down fragments were ligated to the digested pK18mobsacB in one step with the Gibson Assembly kit, and the obtained recombinant plasmid was named pK18-0420;

*Corynebacterium glutamicum* ATCC13032 was transfected with the plasmid pK18-0420 by electroporation, and the electric shock condition was: voltage 1.5 KV, 5 ms, (the width of the electroporation vessel was 1 mm), and the electric shock was performed twice. The first screening of recombinant bacteria was performed on BHI plates containing 25 mg/L kanamycin. The positive recombinants were picked up and further cultured in liquid LB medium overnight, and then the second screening was performed on BHI plates containing 100 g/L sucrose. PCR was performed on the colony by using primers 0420-up-F and 0420-down-R, and a fragment of 1 Kb could be amplified from the 0420 gene knockout recombinant, and the recombinant strain was named as *C. glutamicum* Δ0420. The gene cg0424 was also knocked out by the above method, resulting in a cg0424 single-knockout strain and a cg0420 and cg0424 double-knockout strain, named as *C. glutamicum* Δ0420 and *C. glutamicum* Δ0420 & Δ0424, respectively.

Among them, the primer sequences used were as follows:

```
0420-UP-F:
                                    (SEQ ID NO. 11)
GCAGGTCGACTCTAGAGGATCCAAGTTTCGAACCATGCTTGAAC

0420-UP-R:
                                    (SEQ ID NO. 12)
GATCTGATTCTTCGCACCAATAGGCGACATACCGTTTCTAACTGCTCAG 0420-down-F:
                                    (SEQ ID NO. 13)
CTGAGCAGTTAGAAACGGTATGTCGCCTATTGGTGCGAAGAATCAGATC 0420-down-R:
                                    (SEQ ID NO. 14)
CTATGACCATGATTACGAATTCTGGACCCTAAACTGAGCAGTGA
```

(2) Integration of Genes HasA and VHb

A 500 bp fragment U-up was amplified by PCR, with the genomic DNA of *Corynebacterium glutamicum* ATCC13032 as a template, and using U-up-F and U-up-R as primers, and the PCR product was purified;

A fragment of about 500 bp D-down was amplified by PCR, with the genomic DNA of *Corynebacterium glutamicum* ATCC13032 as a template, and using D-down-F and D-down-R as primers, and the PCR product was purified;

A fragment as shown in SEQ ID NO.10 was amplified by PCR, with the genomic DNA of *Vitreoscilla* (*Vitreoscilla stercoraria* DSM 513) as a template, and using HasA-F and HasA-R as primers, and the PCR product was purified;

The *Corynebacterium glutamicum* suicide plasmid pK18mobsacB was double digested with EcoRI/BamhI, and the fragments U-up, D-down and VHb were ligated to the digested pK18mobsacB in one step with the Gibson Assembly kit, and the obtained recombinant plasmid was named pK18-VHB;

*C. glutamicum* Δ0420 strain, *C. glutamicum* Δ0424 strain and *C. glutamicum*Δ0420 Δ0424 strain constructed in step (I), and wild-type strain were transfected with the plasmid pK18-VHB by electroporation, and the electric shock condition was: voltage 1.5 KV, 5 ms, (the width of the electroporation vessel was 1 mm), and the electric shock was performed twice. The first screening of recombinant bacteria was performed on BHI plates containing 25 mg/L kanamycin. The positive recombinants were picked up and further cultured in liquid LB medium overnight, and then the second screening was performed on BHI plates containing 100 g/L sucrose. PCR was performed on the colony by using primers U-up-F and D-down-R, and a fragment of 1.3 Kb could be amplified from the recombinant integrated with HasA gene, and the obtained recombinant strain was named as *C. glutamicum*-HasA. The above method was also used for the integration of Gene VHb, and the finally obtained strains were *C. glutamicum* Δ0420-HasA-VHB, Δ0424-HasA-VHB, 40420&40424-HasA-VHB and WT-HasA-VHB, respectively.

```
U-up-F:
                                    (SEQ ID NO. 15)
GCAGGTCGACTCTAGAGGATCCTTAGAAGAACTGCTTCTGAAT

U-up-R:
                                    (SEQ ID NO. 16)
AATAGGCATGATATACGCTCCTTCGAACACGGCGACACTGAAC

D-down-F:
                                    (SEQ ID NO. 17)
GTTACCGACGGTTTCTTTCATATTCCAAGCCGGAGAATTTCC
```

-continued

D-down-R:
(SEQ ID NO. 18)
CTATGACCATGATTACGAA ATGAAAGAAACCGTCGGTAAC

HasA-F:
(SEQ ID NO. 19)
AAGGAGCGTATATCATGCCTATTTTCAAGAAGACT

HasA-R:
(SEQ ID NO. 20)
AATAGGCATGATATACGCTCCTTTTATTTAAAAATAGTAACTTTTTT
CTAG (3) Construction of Recombinant Plasmids pXMJ19 Pgm-galU-Ugd and pECXK99E-glmS-glmM-glmU Pseudomonas putida KT2440 was inoculated in 3 ml LB liquid medium and cultured at 30° C. 220 rpm for 24 hours. The bacteria were collected and the genomic DNA was extracted with the cell genome extraction kit. Primers pgm-F/pgm-R, galU-F/galU-R, ugd-F/ugd-R, glmS-F/glmS-R, glmM-F/glmM-R and glmU-F/glmU-R were designed, and the extracted Pseudomonas putida genomic DNA was used as a template to amplify and obtain genes pgm, ugd, galU, glmU, glmS and glmM with the PCR amplification system and procedure. The plasmids pXMJ19 and pECXK99E were enzymatically digested at the selected restriction sites to obtain linear plasmids pXMJ19 and pECXK99E, and Gibson assembly reactions were performed on the amplified fragments pgm, ugd, galU and the linear plasmid pXMJ19, and on glmU, glmS, glmM and the linear plasmid pECXK99E. JM109 competent cells were transformed with the Gibson assembly reaction system. The transformants were selected for plasmid sequencing reaction and sequence alignment, and the recombinant plasmids pXMJ19-pgm-ugd-galU and pECX99E-glmU-glmM-glmS were successfully constructed. The recombinant plasmids were electro-transformed into Corynebacterium glutamicum ATCC13032, C. glutamicumΔ0420-HasA-VHB, Δ0424-HasA-VHB, Δ0420&Δ0424-HasA-VHB and WT-HasA-VHB, strain and the obtained recombinant strain were named as WT, Δ0420, Δ0424 and Δ0420&Δ0424, respectively.

TABLE 1

Primers used for construction of recombinant plasmid pXMJ19-pgm-ugd-galU

| Primer name | Sequence (5'-3') | SEQ ID NO: |
|---|---|---|
| pgm-F | GCATGCCTGCAGGTCGACTCTAGAGGATCCAAGGAGCGTATATCATGACGCTCAGTCCTTTGGC | SEQ ID NO: 21 |
| pgm-R | CTTCATGATATACGCTCCTTTCAGGCAATGGCTTCATCGAC | SEQ ID NO: 22 |
| ugd-F | TCGATGAAGCCATTGCCTGAAAGGAGCGTATATCATGAAGGTCACGGTTTTCGGAAC | SEQ ID NO: 23 |
| ugd-R | GATCATGATATACGCTCCTTTCAAGCTGGCGCAATCTTGC | SEQ ID NO: 24 |
| galU-R | GCAAGATTGCGCCAGCTTGAAAGGAGCGTATATCATGATCAAAAAATGCTTGTTCCCGGCAG | SEQ ID NO: 25 |
| galU-R | CTCATCCGCCAAAACAGCCAAGCTGAATTCTCAGTAAGCCTTGCCAGTCTTG | SEQ ID NO: 26 |

TABLE 2

Primers used for construction of recombinant plasmid pXMJ19-glmU-glmM-glmS

| Primer name | Sequence (5'-3') | SEQ ID NO: |
|---|---|---|
| glmU-F | CAATTTCACACAGGAAACAGACCATGGAATTCAAGGAGCGTATATCATGTCACTCGATATCGTTATTCTCGCC | SEQ ID NO: 27 |
| glmU-R | CGTCGGTACCAAAGTATTTTCTGCTCATTCAGCTCTTCTTGATCTTCTCCG | SEQ ID NO: 28 |
| glmM-P | CGGAGAAGATCAAGAAGAGCTGAAAGGAGCGTATATCATGAGCAGAAAATACTTTGGTACCGACG | SEQ ID NO: 29 |
| glmM-R | GACAGCACCAACGATTCCACACATTCAGACACAAACTTCGCCGACC | SEQ ID NO: 30 |
| glmS-F | CTGGTCGGCGAAGTTTGTGTCTGAAGGAGCGTATATCATGTGTGGAATCGTTGGTGCTG | SEQ ID NO: 31 |
| glmS-R | GCAGGTCGACTCTAGAGGATCCCCGGGTACCTTACTCGACAGTCACCGACTTG | SEQ ID NO: 32 |

Example 2

Production of Hyaluronic Acid by Recombinant Corynebacterium glutamicum

Figure 2:
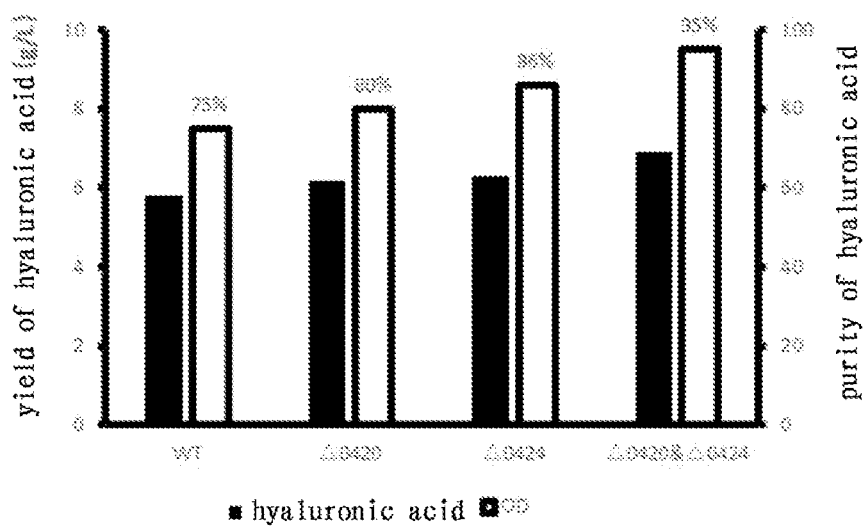
FIG. 2: A graph indicating the yield and product purity of hyaluronic acid by the recombinant *Corynebacterium glutamicum*.

A single clone of each of the constructed recombinant Corynebacterium glutamicum strains WT, Δ0420, Δ0424 and Δ0420&Δ0424 was inoculated in 5 ml BHI medium, at 200 rpm, 30° C. overnight. 10 hours later, 1% of the inoculum was transferred to a 250 ml Erlenmeyer flask (containing 25 ml fermentation medium). 3 hours after incubation at 200 rpm, 28° C., IPTG was added at a final concentration of 0.25 Mm to induce gene expression. The fermentation period was 48 hours. After the fermentation was ended, the supernatant was taken and four times volume of ethanol was added for alcohol precipitation to remove some impurities. After the alcohol precipitation was repeated twice, the content of hyaluronic acid was determined by the sulfuric acid carbazole method. It can be seen from FIG. 2 that both the yield and purity of hyaluronic acid were improved to a certain extent by knocking out cg0420 and cg0420. For the double knockout strain, the yield and purity of hyaluronic acid by shaking bottle were up to 6.9 g/L and 95%, respectively.

Example 3

Figure 3:
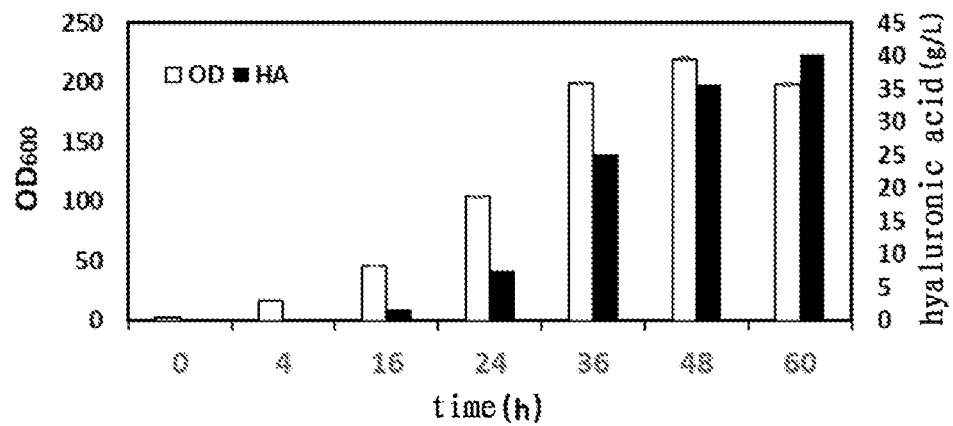
FIG. 3: A graph indicating the yield of hyaluronic acid by the recombinant *Corynebacterium glutamicum* in 5 L fermentation tank.
Figure 4:
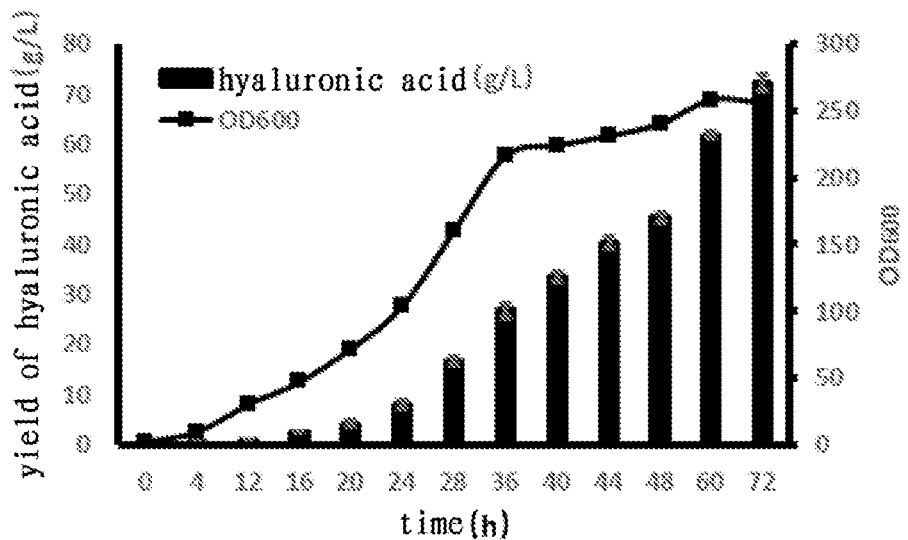
FIG. 4: A graph indicating the yield of hyaluronic acid by the recombinant *Corynebacterium glutamicum* with exogenous addition of hyaluronan hydrolase in 5 L fermentation tank.
Figure 5:
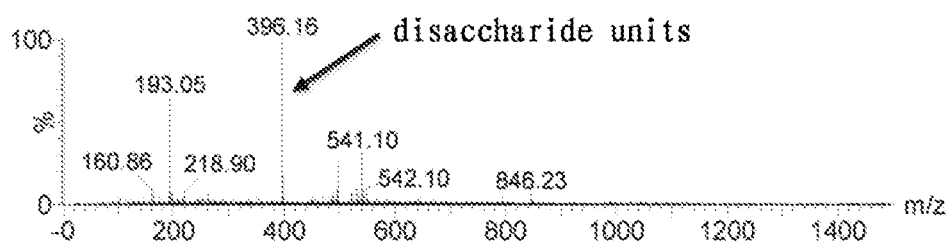
FIG. 5: A mass spectrum of the disaccharide unit of hyaluronic acid produced by the recombinant *Corynebacterium glutamicum*.

Fermentation Culture of Recombinant Corynebacterium glutamicum in 5 L Fermentation Tank A single clone of each of the constructed recombinant Corynebacterium glutamicum strains Corynebacterium glutamicum HasA-VGB/pXMJ19-pgm-ugd-galU and pECX99E-glmU-glmM-glmS (cg0420 and cg0424 knockout) were inoculated in 5 ml BHI medium, at 200 rpm, at 30° C. overnight. 10 hours later, 1% of the inoculum was transferred to a 250 ml Erlenmeyer flask (containing 25 ml fermentation medium). Cultivated at 200 rpm, at 28° C. for 10 hours and 10% of the inoculum was inoculated into the fermentation tank. During the fermentation process, the glucose content in the tank was maintained at about 10 g/L by feeding glucose and pH was controlled to be neutral by feeding NaOH. 20 hours after fermentation, hyaluronic acid hydrolase was added exogenously at a final concentration of 6000 U/mL. The fermentation period was 72 h. It can be seen from FIG. 3 that the OD reached the highest level at 48 h without the addition of hyaluronic acid hydrolase. Hyaluronic acid accumulated rapidly from 24 to 48 hours, and the yield was up to 40 g/L at 60 hours. It can be seen from FIG. 4 that the bacteria were in the logarithmic growth phase from 4 to 36 hours, the bacteria grew rapidly, and entered the stationary phase at 36 hours. Further, hyaluronic acid accumulated rapidly from 24 hours to 60 hours. Compared to FIG. 3, the fermentation period was 12 hours longer, and the yield of hyaluronic acid was also increased significantly. At 72 hours, the yield of hyaluronic acid was up to 72 g/L, which was 32 g/L higher than that without hydrolase, and the OD was also increased to a certain extent.

Comparative Example

Following the same strategy as in Example 1, encoding genes Cgl1118 (NC_003450.3) and Cgl0452 (NC_003450.3) in other pathway competing precursor were knocked out. The recombinant plasmids constructed according to steps (2) and (3) in Example 1 were transformed into the Cgl1118 (NC_003450.3) and Cgl0452 (NC_003450.3) knockout cells. Fermentation was carried out according to the method of Example 2 or 3. The results show that the yield of hyaluronic acid was greatly reduced in these genes knockout strains. The yield by shaking bottle was only 3.1 g/L. The main reason is that knocking out these genes affects the growth of bacteria, resulting in slow growth of the strain. The OD value of fermentation for 48 h was 34, which was only the half of that of the wild type strain cultured under the same conditions.

Although the present invention has been disclosed above with preferred embodiments, it is not intended to limit the present invention. Various changes and modifications can be made by those familiar with this technology, without departing from the spirit and scope of the present invention. Therefore, the protection scope of the present invention should be defined by the claims.

---

What is claimed is:

1. A recombinant *Corynebacterium glutamicum*, wherein exopolysaccharide genes cg0420 and/or cg0424 are/is silenced or knocked out, and hyaluronan synthase is expressed; wherein the hyaluronan synthase comprises the amino acid sequence of SEQ ID NO:3.

2. The recombinant *Corynebacterium glutamicum* according to claim 1, wherein an UDP-N-acetylglucosamine pathway and/or an UDP-glucuronic acid pathway are/is enhanced, wherein the UDP-N-acetylglucosamine pathway comprises: a glutamine-frutose-6-phosphate aminotransferase, a phosphoglucomutase, a UDP-N-acetylglucosamine pyrophosphorylase/glucose-1-phosphate acetyltransferase bifunctional enzyme; and the UDP-glucuronic acid pathway comprises: a phosphoglucomutase, a glucose-6-phosphate uramidotransferase, and a UDP-glucose dehydrogenase.

3. The recombinant *Corynebacterium glutamicum* according to claim 1, wherein the recombinant *Corynebacterium glutamicum* also expresses hemoglobin VHb derived from *Vitreoscilla*.

4. The recombinant *Corynebacterium glutamicum* according to claim 2, wherein genes encoding the UDP-N-acetylglucosamine pathway and/or UDP-glucuronic acid pathway and gene encoding a hemoglobin VHb are ligated to a vector to be expressed in the *Corynebacterium glutamicum*; the vector includes any of the following: pXMJ19, pECXK99E, pEC-XT99A, pEKEx1, pEKEx2, pVWEx1, pVWEx2, pZ8-1, pECTAC-K99 and pAPE12.

5. A method for constructing the recombinant *Corynebacterium glutamicum* according to claim 1, comprising the steps of: (1) knocking out exopolysaccharide synthesis genes cg0420 and cg0424 stepwise or simultaneously by constructing knockout box(es) and recombining the knockout box(es) with genomic genes cg0420 and cg0424 in the *Corynebacterium glutamicum*; and (2) ligating a hyaluronan synthase-encoding gene, a hemoglobin VHb-encoding gene, and at least one gene selected from pgM, ugd, galU, glmS, glmM and glmU to a vector, which is in turn transformed into the cell of the *Corynebacterium glutamicum*, wherein the hyaluronan synthase comprises the amino acid sequence of SEQ ID NO.3.

6. A method for producing hyaluronic acid, comprising steps of fermenting the recombinant *Corynebacterium glutamicum* according to claim 1 in culture media comprising carbon source, nitrogen source, inorganic salts, metal ions and oxygen, wherein the fermentation is performed at 25-35° C. for 24-72 h.

7. The method according to claim 6, wherein a hyaluronan hydrolase or hyaluronan lyase is added in the early stage of the fermentation; and the amount of the added hyaluronan hydrolase or hyaluronan lyase is 500-50000 U/mL.

8. The method according to claim 6, wherein glucose is supplemented during the fermentation process.

9. A method for the preparation of hyaluronic acid and derivative products, comprising steps of fermenting the recombinant *Corynebacterium glutamicum* according to claim 1 in culture media comprising carbon source, nitrogen source, inorganic salts, metal ions and oxygen, and collecting the produced hyaluronic acid and derivative products in the culture media, wherein the fermentation is performed at 25-35° C. for 24-72 h.

* * * * *

UNITED STATES PATENT AND TRADEMARK OFFICE
CERTIFICATE OF CORRECTION

| | | |
|---|---|---|
| PATENT NO. | : 12,054,760 B2 | Page 1 of 1 |
| APPLICATION NO. | : 17/755191 | |
| DATED | : August 6, 2024 | |
| INVENTOR(S) | : Zhen Kang et al. | |

It is certified that error appears in the above-identified patent and that said Letters Patent is hereby corrected as shown below:

In the Specification

In Table 1 on Column 7, there is no sequence ID number listed for the "ugd-F" primer. It currently reads "SEQ ID NO:". This should be changed to "SEQ ID NO: 23"

Signed and Sealed this
Seventeenth Day of September, 2024

Katherine Kelly Vidal
*Director of the United States Patent and Trademark Office*

SEQUENCE LISTING

<160> NUMBER OF SEQ ID NOS: 32

<210> SEQ ID NO 1
<211> LENGTH: 387
<212> TYPE: PRT
<213> ORGANISM: Corynebacterium glutamicum

<400> SEQUENCE: 1

```
Met Ile Leu Arg Asn Arg Ser Arg Cys Arg Ser Ser Arg Glu Asn Val
1               5                   10                  15

Ile Leu Phe Gly Ala Thr Thr Asp Met Ser Asn Ile Phe Tyr Glu Gly
            20                  25                  30

Ile Leu Gln Asn Leu Ile Gln Asp Gly Trp Asp Val His Leu Val Ser
        35                  40                  45

Asn Pro Gly Pro Val Gly Lys Lys Leu Leu Asn Gly Lys Ala His Thr
    50                  55                  60

Ile Glu Met Ser Arg Glu Ile Ser Ile Gly Thr Asp Val Lys Ser Leu
65                  70                  75                  80

Phe Asn Trp Val Leu Leu Arg Lys Ile Arg Pro Arg Val Leu Ile
                85                  90                  95

Val Gly Thr Pro Lys Ala Ser Leu Leu Gly Val Val Ala Ala Arg Ile
                100                 105                 110

Ala Arg Val Pro Arg Ile Val Tyr Val Ala His Gly Leu Arg Ser Glu
            115                 120                 125

Thr Val Leu Gly Leu Lys Lys Lys Ile Leu Val Phe Leu Glu Tyr Leu
    130                 135                 140

Thr Gln Leu Phe Ala His Gln Thr Leu Ala Val Ser His Ser Leu Lys
145                 150                 155                 160

Lys Ala Ile Glu Asp Ala His Pro Arg Phe Lys Gly Arg Val Gln Val
                165                 170                 175

Leu Gly Tyr Gly Ser Met Asn Gly Val Glu Leu Asp Arg Phe Arg Val
            180                 185                 190

Pro Ser Leu Glu Glu Lys Leu Ser Ala Arg Asn Ala Leu Asn Leu Pro
        195                 200                 205

Ser Lys Ser Val Ile Val Gly Phe Val Gly Arg Ile Asn Lys Asp Lys
    210                 215                 220
```

```
Gly Gly Asp Leu Leu Ala Ala Leu Thr Lys His Glu Ala Phe Thr Arg
225                 230                 235                 240

Leu Arg Leu His Leu Leu Ile Ile Gly Glu Leu Glu Asp Asp Asp Leu
            245                 250                 255

Arg Glu Ala Phe Ile Lys Leu Val Asn Glu Gly Gln Val Thr Ile Thr
        260                 265                 270

Gly Trp Ile Asp Phe Pro Glu Pro Leu Ala Ala Val Asp Val Leu
    275                 280                 285

Leu His Pro Thr Gln Arg Glu Gly Leu Gly Met Ser Leu Leu Glu Ala
290                 295                 300

Gln Ala Met Gly Val Pro Val Leu Thr Asn Ala Val Thr Gly Thr Val
305                 310                 315                 320

Asp Ala Val Thr Ser Gly Glu Gly Gly Phe Phe Ala Asp Asp Ser
            325                 330                 335

Val Glu Ser Trp Val Ser Lys Ile Asp Leu Leu Val Ser Asp Pro Lys
            340                 345                 350

Leu Arg Asp Arg Met Gly Arg Ala Gly Arg Gln Phe Val Ser Ala Arg
            355                 360                 365

Phe Asn Arg Asp Asp Val Ala Ala Arg Phe Ser His Phe Val Glu Gln
370                 375                 380

Phe Lys Lys
385

<210> SEQ ID NO 2
<211> LENGTH: 345
<212> TYPE: PRT
<213> ORGANISM: Corynebacterium glutamicum

<400> SEQUENCE: 2

Met Pro Lys Val Ser Val Thr Gly Phe Tyr Asn Arg Cys Glu His
1               5                   10                  15

Leu Glu Arg Thr Ile Glu Ser Ile Leu Asn Gln Thr Tyr Ser Asp Phe
            20                  25                  30

Glu Leu Ile Val Phe Asp Asp Ala Ser Thr Asp Gly Thr Ala Ser Arg
        35                  40                  45

Leu Leu Glu Leu Lys Glu Lys Tyr Asp Asp Pro Arg Phe Arg Phe Ile
50                  55                  60

Ile His Glu Glu Asn Lys Gly Phe Val Lys Gly Leu Ser Glu Ala Ile
65                  70                  75                  80

Ser Gly Ala Lys Gly Gln Tyr Ile Ala Val Gln Gly Ser Gly Asp Val
            85                  90                  95

Ser Leu Pro Arg Arg Leu Glu Leu Gln Val Glu Phe Leu Asp Ala Asn
            100                 105                 110

Pro Ser Val Gly Ala Val Gly Gly Ala Ile Tyr Asn Ile Gln Glu Asp
            115                 120                 125

Thr Gly Thr Arg Asn Pro Gln Arg Phe Glu Lys Pro Ile Ala Thr Phe
            130                 135                 140

Asp Asp Leu Leu Thr Ser Asn Pro Phe Thr His Gly Glu Val Met Tyr
145                 150                 155                 160

Arg Leu Asp Leu Tyr Lys Ser Ile Gly Gly Tyr Arg Ser Gly Phe Thr
            165                 170                 175

Phe Ala Gln Asp Arg Asp Leu Trp Leu Arg Met Ala Lys Lys Ala Asp
            180                 185                 190

Leu Gly Ile Ile Pro Asp Phe Leu Tyr His Arg Tyr Thr Leu Leu Asp
            195                 200                 205
```

-continued

Gly Val Ser Phe Val Pro Asp Lys Thr Ile Arg Gln Arg Cys Phe Ser
        210                 215                 220

Glu Ala Ala Val Arg Leu Ala Leu Met Pro Glu Glu Gly Ala Leu
225                 230                 235                 240

Ala Tyr Ser Arg Leu Glu Ala Glu Gly Pro Thr Ala Val Val Pro Ile
                245                 250                 255

Ala Asp Arg Ala Val Gln Lys Phe Val Pro Lys Ala Ala Ile Arg Leu
            260                 265                 270

Cys Leu Tyr Gly Ala Pro Glu Thr Gly Leu His Met Ala Arg Asp Tyr
        275                 280                 285

Ile Gln Asn Pro Leu Arg Arg Thr Ile Val Val Leu Ile Ser Ile
    290                 295                 300

Tyr Ser Ser Arg Leu Ile Lys Pro Leu Gln Asp Ile Leu Tyr Lys Ser
305                 310                 315                 320

Ile Phe Lys Gly Val Ser Ile Ser Lys Pro Ile Lys Ser Ser Leu Val
                325                 330                 335

Lys Phe Thr Arg Arg Ile Gln Gly Lys
            340                 345

<210> SEQ ID NO 3
<211> LENGTH: 419
<212> TYPE: PRT
<213> ORGANISM: Streptococcus pyogenes

<400> SEQUENCE: 3

Met Pro Ile Phe Lys Lys Thr Leu Ile Val Leu Ser Phe Ile Phe Leu
1               5                   10                  15

Ile Ser Ile Leu Ile Tyr Leu Asn Met Tyr Leu Phe Gly Thr Ser Thr
            20                  25                  30

Val Gly Ile Tyr Gly Val Ile Leu Ile Thr Tyr Leu Val Ile Lys Leu
        35                  40                  45

Gly Leu Ser Phe Leu Tyr Glu Pro Phe Lys Gly Asn Pro His Asp Tyr
    50                  55                  60

Lys Val Ala Ala Val Ile Pro Ser Tyr Asn Glu Asp Ala Glu Ser Leu
65                  70                  75                  80

Leu Glu Thr Leu Lys Ser Val Leu Ala Gln Thr Tyr Pro Leu Ser Glu
                85                  90                  95

Ile Tyr Ile Val Asp Asp Gly Ser Ser Asn Thr Asp Ala Ile Gln Leu
            100                 105                 110

Ile Glu Glu Tyr Val Asn Arg Glu Val Asp Ile Cys Arg Asn Val Ile
        115                 120                 125

Val His Arg Ser Leu Val Asn Lys Gly Lys Arg His Ala Gln Ala Trp
    130                 135                 140

Ala Phe Glu Arg Ser Asp Ala Asp Val Phe Leu Thr Val Asp Ser Asp
145                 150                 155                 160

Thr Tyr Ile Tyr Pro Asn Ala Leu Glu Glu Leu Leu Lys Ser Phe Asn
                165                 170                 175

Asp Glu Thr Val Tyr Ala Ala Thr Gly His Leu Asn Ala Arg Asn Arg
            180                 185                 190

Gln Thr Asn Leu Leu Thr Arg Leu Thr Asp Ile Arg Tyr Asp Asn Ala
        195                 200                 205

Phe Gly Val Glu Arg Ala Ala Gln Ser Leu Thr Gly Asn Ile Leu Val
    210                 215                 220

Cys Ser Gly Pro Leu Ser Ile Tyr Arg Arg Glu Val Ile Ile Pro Asn

```
                225                 230                 235                 240
Leu Glu Arg Tyr Lys Asn Gln Thr Phe Leu Gly Leu Pro Val Ser Ile
                    245                 250                 255
Gly Asp Asp Arg Cys Leu Thr Asn Tyr Ala Ile Asp Leu Gly Arg Thr
                    260                 265                 270
Val Tyr Gln Ser Thr Ala Arg Cys Asp Thr Asp Val Pro Phe Gln Leu
                    275                 280                 285
Lys Ser Tyr Leu Lys Gln Gln Asn Arg Trp Asn Lys Ser Phe Phe Arg
                    290                 295                 300
Glu Ser Ile Ile Ser Val Lys Lys Ile Leu Ser Asn Pro Ile Val Ala
305                 310                 315                 320
Leu Trp Thr Ile Phe Glu Val Val Met Phe Met Leu Ile Val Ala
                    325                 330                 335
Ile Gly Asn Leu Leu Phe Asn Gln Ala Ile Gln Leu Asp Leu Ile Lys
                    340                 345                 350
Leu Phe Ala Phe Leu Ser Ile Ile Phe Ile Val Ala Leu Cys Arg Asn
                    355                 360                 365
Val His Tyr Met Val Lys His Pro Ala Ser Phe Leu Leu Ser Pro Leu
                    370                 375                 380
Tyr Gly Ile Leu His Leu Phe Val Leu Gln Pro Leu Lys Leu Tyr Ser
385                 390                 395                 400
Leu Cys Thr Ile Lys Asn Thr Glu Trp Gly Thr Arg Lys Lys Val Thr
                    405                 410                 415
Ile Phe Lys

<210> SEQ ID NO 4
<211> LENGTH: 545
<212> TYPE: PRT
<213> ORGANISM: Pseudomonas putida KT2440

<400> SEQUENCE: 4

Met Thr Leu Ser Pro Leu Ala Gly Lys Pro Pro Ala Ser Val Leu
1               5                   10                  15
Val Asp Ile Pro Arg Leu Leu Thr Ala Tyr Tyr Thr Gly Arg Pro Asp
                20                  25                  30
Ala Thr Val Ala Ala Gln Arg Val Ala Phe Gly Thr Ser Gly His Arg
                35                  40                  45
Gly Ser Ser Leu Glu Leu Ser Phe Asn Glu Tyr His Val Leu Ala Ile
                50                  55                  60
Ser Gln Ala Ile Cys Leu Tyr Arg Gln Glu Lys Gly Ile Asp Gly Pro
65                  70                  75                  80
Leu Phe Ile Gly Ala Asp Thr His Ala Leu Ser Ala Pro Ala Thr Ala
                    85                  90                  95
Ser Ala Leu Glu Val Leu Ala Ala Asn Gly Val Gln Val Met Leu Ser
                    100                 105                 110
Lys Asp Asp Glu Tyr Thr Pro Thr Pro Ala Val Ser His Ala Ile Leu
                    115                 120                 125
Cys His Asn Arg Gly Arg Thr Gln Gly Leu Ala Asp Gly Ile Val Ile
                    130                 135                 140
Thr Pro Ser His Asn Pro Pro Gln Ser Gly Gly Phe Lys Tyr Asn Pro
145                 150                 155                 160
Pro Asn Gly Gly Pro Ala Asp Ser Asp Val Thr Lys Trp Ile Glu Gly
                    165                 170                 175
Lys Ala Asn Glu Leu Leu Ala Ala Asn Leu Ala Gly Val Lys Arg Met
```

```
                180             185             190
Asp His Ala Gln Ala Leu Gln Ala Pro Thr Thr His Arg His Asp Tyr
            195                 200                 205
Val Ser Asn Tyr Val Ala Asp Leu Glu Asn Val Ile Asp Phe Asp Val
            210                 215                 220
Ile Arg Gly Ala Gly Leu Arg Leu Gly Val Asp Pro Leu Gly Gly Ala
225                 230                 235                 240
Gly Val Arg Tyr Trp Ser Ala Ile Ala Lys His Tyr Gln Leu Asp Leu
                245                 250                 255
Glu Val Val Asn Thr Glu Val Asp Pro Thr Phe Arg Phe Met Thr Val
            260                 265                 270
Asp Trp Asp Gly Gln Ile Arg Met Asp Pro Ser Ser Pro Tyr Ala Met
            275                 280                 285
Gln Gly Leu Ile Gly Leu Arg Glu Arg Phe Asp Val Ala Phe Ala Cys
            290                 295                 300
Asp Pro Asp His Asp Arg His Gly Ile Val Thr Pro Asp Gly Leu Leu
305                 310                 315                 320
Gln Pro Asn Asn Tyr Leu Ala Val Ala Ile Asp Tyr Leu Phe Arg His
                325                 330                 335
Arg Pro Gln Trp Arg Ser Asp Ala Ala Val Gly Lys Thr Val Val Ser
                340                 345                 350
Ser Gly Leu Ile Asp Arg Val Thr Gln Arg Leu Gly Arg Asp Leu Tyr
            355                 360                 365
Glu Val Pro Val Gly Phe Lys Phe Phe Ala Gln Gly Leu Phe Asp Gly
            370                 375                 380
Ser Leu Gly Phe Gly Gly Glu Glu Ser Ala Gly Ala Ser Phe Leu Arg
385                 390                 395                 400
Arg Asp Gly Ser Val Trp Ala Thr Asp Lys Asp Gly Leu Ile Pro Ala
                405                 410                 415
Leu Leu Ala Ala Glu Met Thr Arg Thr Gly Arg Asn Pro Ser Gln
                420                 425                 430
Ala Tyr Ala Asp Leu Thr Glu Ala Leu Gly Lys Pro Phe Ala Thr Arg
            435                 440                 445
Val Glu Ala Lys Ala Asp Ala Arg Gln Lys Ala Leu Leu Ser Lys Leu
            450                 455                 460
Ala Pro Glu Gln Val Lys Ser Thr Glu Leu Ala Gly Glu Pro Ile Val
465                 470                 475                 480
Gln Ile Leu Ser His Ala Pro Gly Asn Gly Gln Ala Ile Gly Gly Leu
                485                 490                 495
Lys Val Met Thr Ala Asn Gly Trp Phe Ala Ala Arg Pro Ser Gly Thr
                500                 505                 510
Glu Asp Ile Tyr Lys Ile Tyr Ala Glu Ser Phe Ile Asp Glu Ala His
            515                 520                 525
Leu Gln Arg Leu Val Glu Glu Ala Gln Val Leu Val Asp Glu Ala Ile
            530                 535                 540
Ala
545

<210> SEQ ID NO 5
<211> LENGTH: 279
<212> TYPE: PRT
<213> ORGANISM: Pseudomonas putida KT2440

<400> SEQUENCE: 5
```

```
Met Ile Lys Lys Cys Leu Phe Pro Ala Ala Gly Tyr Gly Thr Arg Phe
1               5                   10                  15

Leu Pro Ala Thr Lys Ala Met Pro Lys Glu Met Leu Pro Val Val Asn
            20                  25                  30

Lys Pro Leu Ile Gln Tyr Gly Val Glu Glu Ala Leu Asp Ala Gly Leu
            35                  40                  45

Asn Glu Ile Ser Ile Val Thr Gly Arg Gly Lys Arg Ala Leu Glu Asp
50                  55                  60

His Phe Asp Ile Ser Tyr Glu Leu Glu Asn Gln Ile Lys Gly Thr Asp
65                  70                  75                  80

Lys Glu Lys Tyr Leu Val Gly Ile Arg Arg Leu Leu Asn Glu Cys Ser
                85                  90                  95

Phe Ser Tyr Thr Arg Gln Thr Glu Met Lys Gly Leu Gly His Ala Ile
            100                 105                 110

Leu Thr Gly Arg Pro Leu Ile Gly Asp Glu Pro Phe Ala Val Val Leu
            115                 120                 125

Ala Asp Asp Leu Cys Val Asn Pro Glu Gly Asp Gly Val Leu Thr Gln
            130                 135                 140

Met Val Lys Leu Tyr Lys Gln Tyr Arg Cys Ser Ile Val Ala Ile Gln
145                 150                 155                 160

Glu Val Asp Pro Gln Glu Thr Asn Lys Tyr Gly Val Ile Ala Gly Glu
            165                 170                 175

Met Ile Arg Asp Asp Ile Phe Arg Val Thr Asn Met Val Glu Lys Pro
            180                 185                 190

Ala Pro Glu Asp Ala Pro Ser Asn Leu Ala Ile Ile Gly Arg Tyr Ile
            195                 200                 205

Leu Thr Pro Asp Ile Phe Asp Ile Ile Ala Asn Thr Lys Pro Gly Lys
            210                 215                 220

Gly Gly Glu Ile Gln Ile Thr Asp Ala Leu Leu Gln Gln Ala Lys Asp
225                 230                 235                 240

Gly Cys Val Ile Ala Tyr Lys Phe Lys Gly Lys Arg Phe Asp Cys Gly
            245                 250                 255

Gly Ala Glu Gly Tyr Ile Asp Ala Thr Asn Phe Cys Phe Glu Asn Tyr
            260                 265                 270

Tyr Lys Thr Gly Lys Ala Tyr
            275
```

<210> SEQ ID NO 6
<211> LENGTH: 442
<212> TYPE: PRT
<213> ORGANISM: Pseudomonas putida KT2440

<400> SEQUENCE: 6

```
Met Lys Val Thr Val Phe Gly Thr Gly Tyr Val Gly Leu Thr Gln Ala
1               5                   10                  15

Val Cys Leu Ala Gln Val Gly His Ser Val Leu Cys Met Asp Val Asp
            20                  25                  30

Ala Asp Arg Val Ala Ser Leu Ser Glu Gly His Cys Pro Ile Phe Glu
            35                  40                  45

Pro Gly Leu Ala Pro Leu Leu Glu Lys Asn Leu Ala Cys Gly Arg Leu
50                  55                  60

Arg Phe Thr Thr Asp Ala Ala Ala Ala Asn Tyr Ala Arg Leu Gln
65                  70                  75                  80

Phe Ile Ala Val Gly Thr Pro Pro Gln Ala Asp Gly Ser Ala Asp Leu
            85                  90                  95
```

```
Lys His Val Phe Ala Val Val Asp Ser Ile Leu Glu His Ala Asp Gly
                100                 105                 110

Pro Lys Val Ile Val Asn Lys Ser Thr Val Pro Val Gly Thr Val His
            115                 120                 125

Arg Ile Lys Ala Arg Ile Ala Gln Ala Val Ala Asp Thr Ser Arg Phe
        130                 135                 140

Gln Val Ile Ser Asn Pro Glu Phe Leu Lys Glu Gly Ser Ala Val Asp
145                 150                 155                 160

Asp Cys Met Arg Pro Gln Arg Ile Ile Gly Gly Ala Glu Ala Ala
                165                 170                 175

Glu Val Glu Leu Leu Arg Glu Leu Tyr Leu Pro Phe Asn Arg Asn Arg
                180                 185                 190

Glu Lys Phe Met Val Met Asp Ala Arg Ser Ala Glu Leu Thr Lys Tyr
                195                 200                 205

Ala Ala Asn Cys Met Leu Ala Thr Lys Ile Ser Phe Ile Asn Glu Ile
                210                 215                 220

Ala Asn Leu Ala Glu His Leu Gly Ala Asp Ile Glu Met Val Arg Arg
225                 230                 235                 240

Gly Ile Gly Ser Asp Pro Arg Ile Gly Tyr Asp Phe Ile Tyr Ala Gly
                245                 250                 255

Cys Gly Phe Gly Gly Ser Cys Phe Pro Lys Asp Leu Gln Ala Leu Arg
                260                 265                 270

His Ser Ala Glu Ala Glu Gly Phe Glu Thr Gln Leu Leu Arg Ala Val
        275                 280                 285

Glu Ser Val Asn Glu Gln Gln Lys Gly Arg Leu Phe Ser Lys Ile Gln
        290                 295                 300

Arg His Tyr Pro Gly Gly Leu Arg Gly Lys Val Phe Ala Leu Trp Gly
305                 310                 315                 320

Leu Ser Phe Lys Pro Asn Thr Asn Asp Ile Arg Glu Ala Ser Ser Arg
                325                 330                 335

Val Leu Leu Glu Ala Leu Trp Ala Ala Gly Ala Arg Val Gln Ala His
                340                 345                 350

Asp Pro Gln Ala Met Glu Glu Ile Arg Arg His Tyr Gly Pro Arg Ala
                355                 360                 365

Asp Leu Gln Leu Val Pro Cys Lys Asp Ala Leu Arg Gly Ala Asp
        370                 375                 380

Ala Leu Val Ile Val Thr Glu Trp Gln Asp Tyr Arg Val Leu Asn Leu
385                 390                 395                 400

Asp Glu Val Pro Gln Gln Leu Ala Asp Arg Val Val Phe Asp Gly Arg
                405                 410                 415

Asn Leu Tyr Glu Pro Glu His Met Ala Ser Ala Gly Leu Ala Tyr Tyr
                420                 425                 430

Gly Ile Gly Arg Gly Lys Ile Ala Pro Ala
        435                 440

<210> SEQ ID NO 7
<211> LENGTH: 611
<212> TYPE: PRT
<213> ORGANISM: Pseudomonas putida KT2440

<400> SEQUENCE: 7

Met Cys Gly Ile Val Gly Ala Val Ala Glu Arg Asn Ile Thr Ala Ile
1               5                   10                  15

Leu Ile Glu Gly Leu Lys Arg Leu Glu Tyr Arg Gly Tyr Asp Ser Ala
```

```
                    20                  25                  30
Gly Leu Ala Val Leu Thr Gln Asn Gly Glu Leu Gln Arg Arg Arg
                35                  40                  45

Ile Gly Lys Val Ser Glu Leu Glu Val Ala Val Ala Asp Asp Pro Leu
        50                  55                  60

Ala Gly Gln Leu Gly Ile Ala His Thr Arg Trp Ala Thr His Gly Ala
65                  70                  75                  80

Pro Thr Glu Gly Asn Ala His Pro His Phe Ser Gly Asn Asp Val Ala
                85                  90                  95

Val Val His Asn Gly Ile Ile Glu Asn His Glu Glu Leu Arg Glu Glu
                100                 105                 110

Leu Lys Gly Leu Gly Tyr Val Phe Thr Ser Gln Thr Asp Thr Glu Val
            115                 120                 125

Ile Val His Leu Ile His His Thr Leu Lys Ser Ile Pro Asp Leu Thr
            130                 135                 140

Asp Ala Leu Lys Ala Ala Val Lys Arg Leu His Gly Ala Tyr Gly Leu
145                 150                 155                 160

Ala Leu Ile Ser Ala Lys Gln Pro Asp Arg Leu Val Ala Ala Arg Ser
                165                 170                 175

Gly Ser Pro Leu Val Ile Gly Leu Gly Leu Gly Glu Asn Phe Leu Ala
                180                 185                 190

Ser Asp Gln Leu Ala Leu Arg Gln Val Thr Asp Arg Phe Met Tyr Leu
            195                 200                 205

Glu Glu Gly Asp Ile Ala Glu Ile Arg Arg Asp Gln Val Ser Ile Trp
        210                 215                 220

Asp Gln Gln Gly Asn Lys Val Gln Arg Glu Thr Val Gln Tyr His Glu
225                 230                 235                 240

Gly Ala Glu Ala Ala Asp Lys Gly Ala Tyr Arg His Phe Met Leu Lys
                245                 250                 255

Glu Ile His Glu Gln Pro Ser Val Val Gln Arg Thr Leu Glu Gly Arg
            260                 265                 270

Leu Gly Lys Asp Asn Val Leu Val Gln Ala Phe Gly Pro Gln Ala Ala
            275                 280                 285

Asp Leu Phe Ala Lys Val Arg Asn Val Gln Ile Val Ala Cys Gly Thr
        290                 295                 300

Ser Tyr His Ala Gly Met Val Ala Arg Tyr Trp Leu Glu Ser Leu Ala
305                 310                 315                 320

Gly Ile Pro Cys Gln Val Glu Val Ala Ser Glu Phe Arg Tyr Arg Lys
                325                 330                 335

Val Val Val Gln Pro Asp Thr Leu Phe Val Ser Ile Ser Gln Ser Gly
            340                 345                 350

Glu Thr Ala Asp Thr Leu Ala Ala Leu Arg Asn Ala Lys Glu Leu Gly
            355                 360                 365

Phe Leu Gly Ser Leu Ala Ile Cys Asn Val Gly Ile Ser Ser Leu Val
            370                 375                 380

Arg Glu Ser Asp Leu Thr Leu Leu Thr Leu Ala Gly Pro Glu Ile Gly
385                 390                 395                 400

Val Ala Ser Thr Lys Ala Phe Thr Thr Gln Leu Val Ser Leu Met Leu
                405                 410                 415

Leu Thr Leu Ala Leu Gly Gln Val Arg Gly Thr Leu Glu Ala Gly Val
            420                 425                 430

Glu Ala Glu Leu Val Glu Glu Leu Arg Arg Leu Pro Thr Arg Leu Gly
            435                 440                 445
```

-continued

Glu Ala Leu Ala Met Asp Ala Thr Val Glu Lys Ile Ala Glu Leu Phe
        450                 455                 460

Ala Asp Lys His His Thr Leu Phe Leu Gly Arg Gly Ala Gln Tyr Pro
465                 470                 475                 480

Val Ala Met Glu Gly Ala Leu Lys Leu Lys Glu Ile Ser Tyr Ile His
                485                 490                 495

Ala Glu Ala Tyr Pro Ala Gly Glu Leu Lys His Gly Pro Leu Ala Leu
            500                 505                 510

Val Asp Asn Asp Met Pro Val Val Thr Val Ala Pro Asn Asn Glu Leu
        515                 520                 525

Leu Glu Lys Leu Lys Ser Asn Leu Gln Glu Val Arg Ala Arg Gly Gly
    530                 535                 540

Glu Leu Val Val Phe Ala Asp Glu His Ala Gly Met Thr Asn Gly Glu
545                 550                 555                 560

Gly Thr His Val Ile Lys Val Pro His Ile Ala Asp Ala Leu Ala Pro
                565                 570                 575

Ile Leu Tyr Thr Ile Pro Leu Gln Leu Leu Ser Tyr Tyr Val Ala Val
            580                 585                 590

Leu Lys Gly Thr Asp Val Asp Gln Pro Arg Asn Leu Ala Lys Ser Val
        595                 600                 605

Thr Val Glu
    610

<210> SEQ ID NO 8
<211> LENGTH: 446
<212> TYPE: PRT
<213> ORGANISM: Pseudomonas putida KT2440

<400> SEQUENCE: 8

Met Ser Arg Lys Tyr Phe Gly Thr Asp Gly Ile Arg Gly Arg Val Gly
1               5                   10                  15

Glu Tyr Pro Ile Thr Pro Asp Phe Met Leu Lys Leu Gly Trp Ala Ala
            20                  25                  30

Gly Met Ala Phe Arg Lys Gln Gly His Cys Arg Val Leu Val Gly Lys
        35                  40                  45

Asp Thr Arg Ile Ser Gly Tyr Met Phe Glu Ser Ala Leu Glu Ala Gly
    50                  55                  60

Leu Ser Ala Ala Gly Ala Asp Val Met Leu Leu Gly Pro Met Pro Thr
65                  70                  75                  80

Pro Ala Ile Ala Tyr Leu Thr Arg Thr Phe His Ala Glu Ala Gly Ile
                85                  90                  95

Val Ile Ser Ala Ser His Asn Pro His Asp Asp Asn Gly Ile Lys Phe
            100                 105                 110

Phe Ser Gly Gln Gly Thr Lys Leu Pro Asp Glu Val Glu Leu Met Ile
        115                 120                 125

Glu Glu Leu Leu Asp Gln Pro Met Thr Val Val Glu Ser Gly Lys Leu
    130                 135                 140

Gly Lys Val Ser Arg Ile Asn Asp Ala Ala Gly Arg Tyr Ile Glu Phe
145                 150                 155                 160

Cys Lys Ser Ser Val Pro Ser Ser Thr Ser Phe Glu Gly Leu Lys Leu
                165                 170                 175

Val Val Asp Cys Ala His Gly Ala Thr Tyr Lys Val Ala Pro Ser Val
            180                 185                 190

Phe Arg Glu Leu Gly Ala Asp Val Thr Val Leu His Ala Gln Pro Asp

```
                195                 200                 205
Gly Leu Asn Ile Asn Glu Gly Cys Gly Ser Thr His Ile Glu Ser Leu
    210                 215                 220

Gln Ala Ala Val Leu Val Gly His Ala Asp Leu Gly Ile Ala Phe Asp
225                 230                 235                 240

Gly Asp Gly Asp Arg Val Leu Met Val Asp His Thr Gly Ala Ile Val
                245                 250                 255

Asp Gly Asp Glu Leu Leu Phe Ile Ile Ala Arg Asp Leu Gln Glu His
            260                 265                 270

Gly Lys Leu Gln Gly Gly Val Gly Thr Leu Met Ser Asn Leu Gly
        275                 280                 285

Leu Glu Leu Ala Leu Lys Asp Leu Asp Ile Pro Phe Val Arg Ala Lys
290                 295                 300

Val Gly Asp Arg Tyr Val Met Ala Glu Leu Leu Glu Arg Glu Trp Leu
305                 310                 315                 320

Val Gly Gly Glu Asn Ser Gly His Val Val Cys Cys Asn His Thr Thr
                325                 330                 335

Thr Gly Asp Ala Ile Ile Ala Ala Leu Gln Val Leu Met Ala Leu Lys
            340                 345                 350

Arg Arg Gly Glu Thr Leu Ala Gln Ala Arg Gln Ala Leu Arg Lys Cys
        355                 360                 365

Pro Gln Val Leu Ile Asn Val Arg Phe Gly Ala Ser Lys Val Asp Pro
370                 375                 380

Leu Glu His Pro Ala Val Lys Glu Ala Ser Ala Lys Val Thr Glu Ala
385                 390                 395                 400

Leu Ala Gly Arg Gly Arg Val Leu Leu Arg Lys Ser Gly Thr Glu Pro
                405                 410                 415

Leu Val Arg Val Met Val Glu Gly Glu Asp Ser Gln Val Arg Ala
            420                 425                 430

His Ala Glu Ala Leu Ala Lys Leu Val Gly Glu Val Cys Val
        435                 440                 445

<210> SEQ ID NO 9
<211> LENGTH: 455
<212> TYPE: PRT
<213> ORGANISM: Pseudomonas putida KT2440

<400> SEQUENCE: 9

Met Ser Leu Asp Ile Val Ile Leu Ala Ala Gly Gln Gly Thr Arg Met
1               5                   10                  15

Arg Ser Ala Leu Pro Lys Val Leu His Pro Val Ala Gly Asn Ser Met
                20                  25                  30

Leu Gly His Val Ile His Ser Ala Arg Gln Leu Gln Pro Gln Gly Ile
            35                  40                  45

His Val Val Ile Gly His Gly Ala Glu Leu Val Arg Glu Arg Leu Ala
        50                  55                  60

Ala Asp Asp Leu Asn Phe Val Met Gln Asp Lys Gln Leu Gly Thr Gly
65                  70                  75                  80

His Ala Val Ala Gln Ala Leu Pro Ala Leu Thr Ala Asp Thr Val Leu
                85                  90                  95

Val Leu Tyr Gly Asp Val Pro Leu Ile Glu Val Glu Thr Leu Gln Arg
            100                 105                 110

Leu Leu Ala Lys Ala Asn Asp Gln Gln Leu Gly Leu Leu Thr Val Thr
        115                 120                 125
```

```
Leu Asp Asp Pro Thr Gly Tyr Gly Arg Ile Val Arg Asp Glu Gln Gly
    130                 135                 140
Lys Val Thr Ala Ile Val Glu His Lys Asp Ala Asn Asp Ala Gln Lys
145                 150                 155                 160
Ala Ile Lys Glu Gly Asn Thr Gly Ile Leu Ala Leu Pro Ala Ala Arg
                165                 170                 175
Leu Ala Asp Trp Met Gly Arg Leu Ser Asn Asn Asn Ala Gln Gly Glu
            180                 185                 190
Tyr Tyr Leu Thr Asp Val Ile Ala Met Ala Val Ala Asp Gly Leu Val
        195                 200                 205
Val Ala Thr Glu Gln Pro His Asp Ala Met Glu Val Gln Gly Ala Asn
210                 215                 220
Asp Arg Arg Gln Leu Ser Glu Leu Glu Arg His Tyr Gln Leu Arg Glu
225                 230                 235                 240
Gly Arg Arg Leu Met Ala Gln Gly Val Thr Leu Arg Asp Pro Ala Arg
                245                 250                 255
Phe Asp Val Arg Gly Glu Val Ser Val Gly Arg Asp Val Leu Ile Asp
            260                 265                 270
Ile Asn Val Ile Leu Glu Gly Lys Val Ile Glu Asp Asp Val Gln
        275                 280                 285
Ile Gly Pro Asn Cys Val Ile Lys Asn Thr Thr Leu Arg Lys Gly Ala
290                 295                 300
Val Val Lys Ala Asn Ser His Leu Glu Gly Ala Val Met Gly Glu Gly
305                 310                 315                 320
Ser Asp Ala Gly Pro Phe Ala Arg Leu Arg Pro Gly Ser Val Leu Asp
                325                 330                 335
Ala Lys Ala His Val Gly Asn Phe Val Glu Leu Lys Asn Ala His Leu
            340                 345                 350
Gly Glu Gly Ala Lys Ala Gly His Leu Thr Tyr Leu Gly Asp Ala Glu
        355                 360                 365
Ile Gly Ala Arg Thr Asn Ile Gly Ala Gly Thr Ile Thr Cys Asn Tyr
370                 375                 380
Asp Gly Ala Asn Lys Phe Lys Thr Val Met Gly Glu Asp Val Phe Ile
385                 390                 395                 400
Gly Ser Asn Asn Ser Leu Val Ala Pro Val Glu Ile Lys Ala Gly Ala
                405                 410                 415
Thr Thr Ala Ala Gly Ser Thr Ile Thr Gln Ala Val Glu Ala Gly Asp
            420                 425                 430
Leu Ala Val Ala Arg Ala Arg Gln Arg Asn Ile Ser Gly Trp Lys Arg
        435                 440                 445
Pro Glu Lys Ile Lys Lys Ser
    450                 455

<210> SEQ ID NO 10
<211> LENGTH: 146
<212> TYPE: PRT
<213> ORGANISM: Vitreoscilla

<400> SEQUENCE: 10

Met Leu Asp Gln Gln Thr Ile Asn Ile Ile Lys Ala Thr Val Pro Val
1               5                   10                  15
Leu Lys Glu His Gly Val Thr Ile Thr Thr Thr Phe Tyr Lys Asn Leu
            20                  25                  30
Phe Ala Lys His Pro Glu Val Arg Pro Leu Phe Asp Met Gly Arg Gln
        35                  40                  45
```

```
Glu Ser Leu Glu Gln Pro Lys Ala Leu Ala Met Thr Val Leu Ala Ala
    50                  55                  60

Ala Gln Asn Ile Glu Asn Leu Pro Ala Ile Leu Pro Ala Val Lys Lys
 65                  70                  75                  80

Ile Ala Val Lys His Cys Gln Ala Gly Val Ala Ala His Tyr Pro
                 85                  90                  95

Ile Val Gly Gln Glu Leu Leu Gly Ala Ile Lys Glu Val Leu Gly Asp
            100                 105                 110

Ala Ala Thr Asp Asp Ile Leu Asp Ala Trp Gly Lys Ala Tyr Gly Val
        115                 120                 125

Ile Ala Asp Val Phe Ile Gln Val Glu Ala Asp Leu Tyr Ala Gln Ala
    130                 135                 140

Val Glu
145

<210> SEQ ID NO 11
<211> LENGTH: 44
<212> TYPE: DNA
<213> ORGANISM: Artificial Sequence
<220> FEATURE:
<223> OTHER INFORMATION: Primer 0420-UP-F used for the construction of
      the recombinant Corynebacterium glutamicum

<400> SEQUENCE: 11
gcaggtcgac tctagaggat ccaagtttcg aaccatgctt gaac                    44

<210> SEQ ID NO 12
<211> LENGTH: 49
<212> TYPE: DNA
<213> ORGANISM: Artificial Sequence
<220> FEATURE:
<223> OTHER INFORMATION: Primer 0420-UP-R used for the construction of
      the recombinant Corynebacterium glutamicum

<400> SEQUENCE: 12
gatctgattc ttcgcaccaa taggcgacat accgtttcta actgctcag               49

<210> SEQ ID NO 13
<211> LENGTH: 49
<212> TYPE: DNA
<213> ORGANISM: Artificial Sequence
<220> FEATURE:
<223> OTHER INFORMATION: Primer 0420-down-F used for the construction of
      the recombinant Corynebacterium glutamicum

<400> SEQUENCE: 13
ctgagcagtt agaaacggta tgtcgcctat tggtgcgaag aatcagatc               49

<210> SEQ ID NO 14
<211> LENGTH: 44
<212> TYPE: DNA
<213> ORGANISM: Artificial Sequence
<220> FEATURE:
<223> OTHER INFORMATION: Primer 0420-down-R used for the construction of
      the recombinant Corynebacterium glutamicum

<400> SEQUENCE: 14
ctatgaccat gattacgaat tctggaccct aaactgagca gtga                    44

<210> SEQ ID NO 15
<211> LENGTH: 43
<212> TYPE: DNA
<213> ORGANISM: Artificial Sequence
```

<220> FEATURE:
<223> OTHER INFORMATION: Primer U-up-F used for the construction of the
      recombinant Corynebacterium glutamicum

<400> SEQUENCE: 15
gcaggtcgac tctagaggat ccttagaaga actgcttctg aat                          43

<210> SEQ ID NO 16
<211> LENGTH: 43
<212> TYPE: DNA
<213> ORGANISM: Artificial Sequence
<220> FEATURE:
<223> OTHER INFORMATION: Primer U-up-R used for the construction of the
      Recombinant Corynebacterium glutamicum

<400> SEQUENCE: 16
aataggcatg atatacgctc cttcgaacac ggcgacactg aac                          43

<210> SEQ ID NO 17
<211> LENGTH: 42
<212> TYPE: DNA
<213> ORGANISM: Artificial Sequence
<220> FEATURE:
<223> OTHER INFORMATION: Primer D-down-F used for the construction of
      the recombinant Corynebacterium glutamicum

<400> SEQUENCE: 17
gttaccgacg gtttctttca tattccaagc cggagaattt cc                           42

<210> SEQ ID NO 18
<211> LENGTH: 40
<212> TYPE: DNA
<213> ORGANISM: Artificial Sequence
<220> FEATURE:
<223> OTHER INFORMATION: Primer D-down-R used for the construction of
      the recombinant Corynebacterium glutamicum

<400> SEQUENCE: 18
ctatgaccat gattacgaaa tgaaagaaac cgtcggtaac                              40

<210> SEQ ID NO 19
<211> LENGTH: 35
<212> TYPE: DNA
<213> ORGANISM: Artificial Sequence
<220> FEATURE:
<223> OTHER INFORMATION: Primer HasA-F used for the construction of the
      Recombinant Corynebacteerium glutamicum

<400> SEQUENCE: 19
aaggagcgta tatcatgcct attttcaaga agact                                   35

<210> SEQ ID NO 20
<211> LENGTH: 52
<212> TYPE: DNA
<213> ORGANISM: Artificial Sequence
<220> FEATURE:
<223> OTHER INFORMATION: Primer HasA-R used for the construction of the
      recombinant corynebacterium glutamicum

<400> SEQUENCE: 20
aataggcatg atatacgctc cttttattta aaatagtaa cttttttttct ag                52

<210> SEQ ID NO 21
<211> LENGTH: 64
<212> TYPE: DNA
<213> ORGANISM: Artificial Sequence
<220> FEATURE:

<223> OTHER INFORMATION: Primer pgm-F used for construction of
recombinant plasmid pXMJ19-pgm-ugd-galU

<400> SEQUENCE: 21
gcatgcctgc aggtcgactc tagaggatcc aaggagcgta tcatgacg ctcagtcctt    60 tggc                                                                64

<210> SEQ ID NO 22
<211> LENGTH: 41
<212> TYPE: DNA
<213> ORGANISM: Artificial Sequence
<220> FEATURE:
<223> OTHER INFORMATION: Primer pgm-R used for construction of
recombinant plasmid pXMJ19-pgm-ugd-galU

<400> SEQUENCE: 22
cttcatgata tacgctcctt tcaggcaatg gcttcatcga c                      41

<210> SEQ ID NO 23
<211> LENGTH: 57
<212> TYPE: DNA
<213> ORGANISM: Artificial Sequence
<220> FEATURE:
<223> OTHER INFORMATION: Primer ugd-F used for construction of
recombinant plasmid pXMJ19-pgm-ugd-galU

<400> SEQUENCE: 23
tcgatgaagc cattgcctga aaggagcgta tcatgaag gtcacggttt tcggaac       57

<210> SEQ ID NO 24
<211> LENGTH: 40
<212> TYPE: DNA
<213> ORGANISM: Artificial Sequence
<220> FEATURE:
<223> OTHER INFORMATION: Primer ugd-R used for construction of
recombinant plasmid pXMJ19-pgm-ugd-galU

<400> SEQUENCE: 24
gatcatgata tacgctcctt tcaagctggc gcaatcttgc                        40

<210> SEQ ID NO 25
<211> LENGTH: 62
<212> TYPE: DNA
<213> ORGANISM: Artificial Sequence
<220> FEATURE:
<223> OTHER INFORMATION: Primer galU-F used for construction of
recombinant plasmid pXMJ19-pgm-ugd-galU

<400> SEQUENCE: 25
gcaagattgc gccagcttga aaggagcgta tcatgatc aaaaaatgct tgttcccggc    60
ag                                                                 62

<210> SEQ ID NO 26
<211> LENGTH: 52
<212> TYPE: DNA
<213> ORGANISM: Artificial Sequence
<220> FEATURE:
<223> OTHER INFORMATION: Primer galU-R used for construction of
recombinant plasmid pXMJ19-pgm-ugd-galU

<400> SEQUENCE: 26
ctcatccgcc aaaacagcca agctgaattc tcagtaagcc ttgccagtct tg          52

<210> SEQ ID NO 27
<211> LENGTH: 73

```
<212> TYPE: DNA
<213> ORGANISM: Artificial Sequence
<220> FEATURE:
<223> OTHER INFORMATION: Primer glmU-F used for construction of
      recombinant plasmid pXMJ19-glmU-glmM-glmS

<400> SEQUENCE: 27
caatttcaca caggaaacag accatggaat tcaaggagcg tatatcatgt cactcgatat      60
cgttattctc gcc                                                        73

<210> SEQ ID NO 28
<211> LENGTH: 51
<212> TYPE: DNA
<213> ORGANISM: Artificial Sequence
<220> FEATURE:
<223> OTHER INFORMATION: Primer glmU-R used for construction of
      recombinant plasmid pXMJ19-glmU-glmM-glmS

<400> SEQUENCE: 28
cgtcggtacc aaagtatttt ctgctcattc agctcttctt gatcttctcc g              51

<210> SEQ ID NO 29
<211> LENGTH: 65
<212> TYPE: DNA
<213> ORGANISM: Artificial Sequence
<220> FEATURE:
<223> OTHER INFORMATION: Primer glmM-F used for construction of
      recombinant plasmid pXMJ19-glmU-glmM-glmS

<400> SEQUENCE: 29
cggagaagat caagaagagc tgaaaggagc gtatatcatg agcagaaaat actttggtac     60
cgacg                                                                 65

<210> SEQ ID NO 30
<211> LENGTH: 46
<212> TYPE: DNA
<213> ORGANISM: Artificial Sequence
<220> FEATURE:
<223> OTHER INFORMATION: Primer glmM-R used for construction of
      recombinant plasmid pXMJ19-glmU-glmM-glmS

<400> SEQUENCE: 30
gacagcacca acgattccac acattcagac acaaacttcg ccgacc                    46

<210> SEQ ID NO 31
<211> LENGTH: 59
<212> TYPE: DNA
<213> ORGANISM: Artificial Sequence
<220> FEATURE:
<223> OTHER INFORMATION: Primer glmS-F used for construction of
      recombinant plasmid pXMJ19-glmU-glmM-glmS

<400> SEQUENCE: 31
ctggtcggcg aagtttgtgt ctgaaggagc gtatatcatg tgtggaatcg ttggtgctg      59

<210> SEQ ID NO 32
<211> LENGTH: 53
<212> TYPE: DNA
<213> ORGANISM: Artificial Sequence
<220> FEATURE:
<223> OTHER INFORMATION: Primer glmS-R used for construction of
      recombinant plasmid pXMJ19-glmU-glmM-glmS

<400> SEQUENCE: 32
gcaggtcgac tctagaggat ccccgggtac cttactcgac agtcaccgac ttg            53
```